United States Patent [19]

Schick et al.

[11] Patent Number: 4,808,534

[45] Date of Patent: Feb. 28, 1989

[54] METHOD AND APPARATUS FOR THE MICROBIOLOGICAL PRODUCTION OF SINGLE-CELL PROTEIN

[76] Inventors: Josef H. Schick, Mozartstr 10, 5000 Koeln 70, Fed. Rep. of Germany; Josû Garrido Màrquez, Gral. Pardinas 82, Madrid, Spain

[21] Appl. No.: 885,957

[22] Filed: Jul. 15, 1986

Related U.S. Application Data

[63] Continuation of Ser. No. 293,929, Aug. 18, 1981, abandoned, which is a continuation of Ser. No. 169,369, Jul. 16, 1980, abandoned, which is a continuation of Ser. No. 868,430, Jan. 10, 1978, abandoned.

[30] Foreign Application Priority Data

Jan. 10, 1977 [DE] Fed. Rep. of Germany ....... 2700698
Jan. 10, 1977 [DE] Fed. Rep. of Germany ....... 2700697

[51] Int. Cl.$^4$ .............................................. C12N 1/32
[52] U.S. Cl. .................... 435/247; 435/255; 435/313; 435/940
[58] Field of Search ................. 435/68, 243, 246–247, 435/313–316, 812, 818

[56] References Cited

U.S. PATENT DOCUMENTS

| | | | |
|---|---|---|---|
| 3,057,785 | 10/1962 | Olsen | 435/313 X |
| 3,274,075 | 9/1966 | Kersting | 435/316 |
| 3,847,748 | 11/1974 | Gibson et al. | 435/313 X |
| 3,954,565 | 5/1976 | Boiko et al. | 435/316 X |
| 3,985,622 | 10/1976 | Hawkins | 435/316 X |
| 4,036,699 | 7/1977 | Quigg | 435/818 X |
| 4,041,180 | 8/1977 | Wilson | 435/246 |

*Primary Examiner*—R. B. Penland
*Attorney, Agent, or Firm*—Klauber & Jackson

[57] ABSTRACT

Method and apparatus is described for the microbiological production of single-cell protein making use of ethanol as a base material thereby allowing the protein produced to be used for human consumption.

The process involves the cultivation of ethanol activated yeasts at temperatures between 20° and 40° C. under aerobic conditions in a fermentation column containing a dilute nutrient medium having a pH value in the range 2.5 to 5 containing nutrient salts, acid phosphate and nitrogen-containing substances in which the nutrient medium is continuously circulated into and through and out of the fermentation column and at each re-entry into the column is introduced tangentially into a zone which is oxygen enriched using oxygen gas molecules in the range 1 to 7 mu to form a bio-mass which can be separated and dried to form a protein product.

The formation of a large gas bubble in the fermentation column is prevented by carrying the process out under a positive pressure and a gas extraction stage is provided immediately beyond the column. Pure oxygen or oxygen-enriched air may be used.

In apparatus for performing the above method the pump for circulating the medium from the heat exchanger to the column is located in a conduit between the heat exchanger and the column.

Dispersion of the oxygen or oxygen-enriched air is achieved by one or more sintered plates.

22 Claims, 1 Drawing Sheet

METHOD AND APPARATUS FOR THE MICROBIOLOGICAL PRODUCTION OF SINGLE-CELL PROTEIN

This is a continuation of application Ser. No. 293,929, filed Aug. 18, 1981, now abandoned which is in turn, a continuation of Ser. No. 169,369, filed July 16, 1980, now abandoned, which is in turn a continuation of application Ser. No. 868,430, filed Jan. 10, 1978, now abandoned.

FIELD OF THE INVENTION

The invention concerns processes and apparatus for the microbiological production of single-cell protein, in particular making use of ethanol.

BACKGROUND TO THE INVENTION

As a result of the ever-increasing population there has arisen a growing need for high-value nourishment. Accordingly, there is an increasing interest in the production of protein from hydrocarbons. The method of producing protein-products is the microbiological production of single cell protein (SCP for short) by cultivating SCP forming micro-organisms such as yeasts or bacteria. To this end several processes have already been put forward for the carrying out of biological fermentation processes, and various raw materials have been tried out as substrates for the production of SCP. Carbohydrate-waste products from industry have already been utilised, such as molasses, sawdust from woodworkings, and sulphite-liquor which occurs in the cellulose industry.

More recent processes use as substrates products obtained from oil. Micro-organisms have been discovered which can live on crude-oil, n-paraffins, methane, methanol and ethanol. However, the production of SCP of the quality required for foods has so far given considerable difficulty. In employing n-paraffins as substrates, bacteria are widely used which give rise to insuperable problems in the control of the process and the danger of infection in the culture-medium. There are, furthermore, difficulties in the homogeneous preservation of the four-fold mixture of n-paraffin, water, air (or oxygen) and solid. The substrate raw materials oil and n-paraffin, moreover, contain toxic materials which must be removed, by means of costly purification processes, either from the substrate itself or from the end product, the bio-mass. Complete purification and the production of a bio-mass which contains no trace of this kind of undesirable material are however impossible to achieve in practice. Thus, until now, the admissibility of such SCP products as foodstuffs has been resisted by official bodies and consumer organisations.

PRIOR ART

As a means of overcoming these difficulties it has already been suggested that methanol and ethanol should be used as substrates for the production of SCP. Bio-synthetic processes are known whereby certain bacterial strains, such as the strains Methylomonas species, *Methylomonas methanolica, Methylotrophic bacterium, Pseudomonas methanica,* and also bacterial strains of the families Bacillus, Actinomyces, Protaminobacter, Micrococcus, Corynebacterium etc., are propagated by fermentation in a synthetic cultivating medium which contains methanol as its sole or predominant source of carbon.

Another possibility is the use of yeasts on substrates containing methanol or ethanol, whereby, in particular, Candida-yeasts are employed.

From both these kinds of process one obtains substrate yields of between 40 and 45%, of which the oxygen yield comprises some 20–25%. The protein content of the manufactured protein products amounts to about 60% with the use of yeasts, and about 80% with the use of bacteria.

If methanol is used as substrate the resultant bio-mass is usable only as animal-feed, so long as the official ban on its use as a human foodstuff lasts. The use of bacteria gives rise, moreover, to a considerable danger of infection from foreign bacteria, which is further assisted by the fact that processes of this kind take place in a pH value of 6 to 7. This pH-range provides the foreign bacteria with ideal growth conditions. The use of yeasts, particularly certain yeasts of the sub-families Saccharomycesoideae and Cryptococcoideae, which have been admitted by the American Food and Drug Administration for direct use in certain foodstuffs for human use, on ethanol as substrate, makes possible the production of SCP which is suitable for direct use by humans as a foodstuff.

OBJECT OF THE INVENTION

An object of the invention is to provide a process of the above type which, compared with existing processes, produces higher yields of substrate and oxygen and leads to SCP products of greater purity.

It is another object to provide apparatus within which such improved processes can be carried out.

THE INVENTION

This object is achieved by a process for the microbiological production of single-cell protein using an ethanol base, in which ethanol-activated yeasts are cultivated at temperatures of between 20° and 40° C., under aerobic conditions in a fermentation column in the presence of ethanol and oxygen, in a dilute nutrient medium having a pH value of between 2.5 and 4, which contains nutrient salts, acid phosphate and a nitrogen containing substance, and the bio-mass thus cultivated is separated and dried to form a protein product wherein, according to the invention, the nutrient medium is continuously circulated into and through and out of the column and at each re-entry into the column is introduced tangentially into a zone which is enriched with oxygen gas dispersed to between 1 and 7 mu.

Preferably the bio-mass is caused to pass through the fermentation column without the formation of large gas bubbles and its gas content is extracted outside the fermentation column. Preferably the period of time spent by the gas-liquid-solid mixture during each pass through the fermentation column lies in the range 0.2 to 1.0 $h^{-1}$.

In order to prevent the formation of foam and a gas bubble rising above the mixture, the latter passes through the fermentation zone under a definite pressure so that any gas bubbles which are formed are immediately drawn along and led off from the fermentation column before foam can form.

It is expedient to use pure oxygen. The higher costs thus incurred are outweighed by the advantages which result. For example, the absence of nitrogen causes a reduction in the formation of foam which otherwise would have to be led off. Also the waste gas will only consist of carbon dioxide and unused oxygen. Furthermore, the protein-containing end product does not need to be subjected to any additional purification processes. An oxygen purity of 95% is sufficient.

It is possible to use oxygen enriched air and a moisture content in the oxygen does not give trouble.

It is also expedient to cool the bio-mass after it has been withdrawn from the fermentation area. To this end it is passed into a heat exchange zone from the upper region of which the gas is extracted.

It is advantageous, with the process according to the invention, to employ a pH value for the nutrient medium of 3.5, and it has been proved to be particularly effective if the oxygen-enriching process is done with oxygen dispersed to 3 mu.

The process according to the invention has the advantage of producing high yields of substrate, of between 70 and 80%, and high yields of oxygen, reaching 80% and more, together with SCP products of the highest purity.

According to the invention the nutrient medium is subjected to brisk movement in a circular course. This has the effect of preventing the formation of a gas bubble in the fermentation column, gas bubbles of oxygen and carbon dioxide being immediately removed from the fermentation column.

The process according to the invention incorporates an aerobic fermentation process, by which micro-organisms multiply in a nutrient medium consisting essentially of ethanol as the source of carbon, and thereby a precise gas-liquid distribution and mixing effect between the nutrient medium and the oxygen introduced to enrich the nutrient medium is maintained.

It was surprisingly discovered that by enriching the nutrient solution as it is introduced tangentially into the enriching chamber with ultra-fine oxygen bubbles of the order of approximately 1 to 7 mu, preferably 3 mu, a stable dispersion of gas-liquid-solid is allowed to form which can be conducted through the fermentation chamber at a relatively high speed without breaking up and without the appearance of a troublesome development of foam associated with existing processes of this kind. It was further found that the yeast grown is optimised in the medium thus dispersed, and leads, in contrast to the existing state of the technology, to surprisingly high yields from substrate and oxygen. The process according to the invention can be carried out with numerous yeast strains.

Yeasts which can be used to advantage are, for example, sporogenous yeasts, which, as a consequence of their high dehydrogenate-alcohol level, can breed in media with a relatively high concentration of ethanol, such as the species *S. cheresiensis, S. beticus, S. montuliensis* and *S. rouxii*, as well as bakers' yeasts, such as various strains of the species *S. cerevisiae*. It is also possible to make use, on various nutrient bases, of yeasts which are known to be particularly suitable for this purpose, such as the species *Hansenula anomala, Candida utulis* and Rhodotorula Glutinis, as well as certain types of Candida, such as *Candida curvata, Candida lipolytica, Candida pulcherima, Candida parapsilosis,* certain types of Hansenula, such as *Hansenula miso, Hansenula wickerhamii,* types of Saccharomyces, such as *Saccharomyces carlsbergensis, Saccharomyces cerevisiae, Saccharomyces fragilis* and types of Pichia, such as *Pichia pastoris* and *Pichia haplophyla*. All the yeasts used convert ethanol as the source of carbon into acceptable yields. Among these the yeast *Hansenula anomala* (strain 926) has proved successful in respect of ethanol yield, speed of growth and the particularly high quality of the protein product which can be obtained.

The ethanol used can be natural or synthetic in origin and can, for example, be obtained by the addition of water to pure ethylene. The ethanol is added to the culture medium in relatively high concentration. This concentration comprises preferably 1% to 13% but ideally 10%, the upper limit being determined by the highest concentration which can be tolerated by the yeast cells typically 15% to 20%.

Culture media normally employed contain in usable form assimilable sources of nitrogen, mineral salts, e.g. phosphorus-, magnesium-, calcium-, potassium-, sulphur-, and sodium-containing salts such as copper, manganese, molybdenum, zinc, iron, boron, iodine or similarly endowed trace minerals. The relative quantities of these nutrient materials can vary, in a manner already known, in accordance with the special micro-organism used. In addition to this, the nutrient medium can contain vitamins, in a known manner, if their presence is required for the development of the micro-organism. In the preferred culture media to be used the following ingredients can, as an example, be present in the stated quantities:

| | |
|---|---|
| Acid potassium-phosphate, or a corresponding quantity of phosphoric acid | 0.02 to 0.2% |
| Ammonium-sulphate, or a quantity of urea giving the corresponding quantity of nitrogen | 0.02 to 1.0% |
| Magnesium-sulphate | 0.01 to 1.0% |
| Other growth factors | 0.1 to 10.0% |

The other growth factors include, for example, NaCl, KCl, $CaCl_2$, Kl, $FeCl_3$, $ZnSO_4$, $MnSO_4$, $CoCl_2$ and $H_3PO_3$.

Examples of nitrogen sources are secondary inorganic salts of ammonia like ammonium-sulphate, ammonium-phosphate, ammonium-chloride and ammonium-nitrate, as well as organic nitrogen compounds like urea and amino-acids.

The culture takes place at temperatures of approximately 20° C. to 40° C., and within a pH range of approximately 2.5 to 4, ideally at 35° C. and pH 3.5 respectively.

According to the invention, the required relative movement of the flowing medium and the introduced oxygen is preferably effected by the tangential introduction of the culture liquid, moving in a circular direction, to the oxygen which is injected upwardly from below.

The micro-organisms can be separated from the culture medium in accordance with known processes, e.g. by centrifuging or filtering off, if necessary in combination with a flocculation stage. The end product occurs in such high purity that, after simple washing and drying, it can be used directly for the desired purpose.

The invention also includes apparatus for carrying out the process described above in which there is a fermentation column and components, with inlets for nutrient solution, inoculation material and oxygen, and outlets for the bio-mass and exhaust air, together with, if desired, an inlet or inlets for auxiliary materials and a sampling valve, together with a pumping device which causes the circulatory movement of the culture medium.

The apparatus according to the invention is thereby characterised in that the fermentation column is connected by conduits to a separate heat exchanger; the pump which causes the circulation of the culture medium through the fermentation column, an upper conduit, the heat exchanger and through a lower conduit, is arranged inside the lower conduit; a gas-flow separator having pore sizes of 1 to 7 mu is located above the oxygen inlet entering the column at floor level, and the lower conduit is in the form of a tangential liquid inlet and is arranged so that it enters the column slightly above the gas-flow separator; a gas-extraction chamber is situated (in the direction of circulation) between the column and the heat exchanger, and the upper conduit is in the form of a vertical liquid inlet and is arranged so that it enters the gas extraction chamber downwardly from above.

Such apparatus permits the gas-enrichment of the nutrient solution, which leads to an outstanding distribution of gas-liquid-solid, and has such a good mixing effect that the mixture in circulation remains essentially homogeneous, and the formation of foam is vigorously prevented. The formation of foam is almost completely prevented by locating the gas extraction chamber between the fermentation column and the heat exchanger (as viewed in the direction of circulation) and by constructing the upper conduit between the fermentation column and the heat exchanger in the form of a vertical liquid inlet entering the gas extraction chamber downwardly from above. Unused oxygen and carbon dioxide occurring during the fermentation process are removed from the liquid culture-medium and are extracted as exhaust air by means of this gas-extraction chamber. The otherwise troublesome formation of foam is thus safely prevented.

Preferably the pump is operated with such power that, by means of the resultant pressure, any gases possibly occurring in the fermentation column are immediately expelled from it and allowed to expand only in the gas-extraction chamber under foam formation. The fermentation column is operated so that it is always completely filled with liquid so that the formation of a gas bubble is prevented.

It has been shown to be advantageous to construct the gas-stream separator out of one or more sintered-plates.

It is also advantageous if the gas-extraction chamber is arranged in the heat exchanger itself above the heat exchanger assembly. In this way it follows that the bio-mass left after the extraction of gas, runs through the heat exchanger from top to bottom by virtue of its own weight.

The extraction of the bio-mass after its passage through the heat exchanger has been improved by connecting the bio-mass outlet directly to the lower conduit, downstream from the pump. In this way the full pressure of the pump is also available at the bio-mass outlet.

For practical purposes the conduit for the nutrient solution is connected to the section of the lower conduit rising to the fermentation column, at a distance from the bio-mass outlet. Between the outlet and the inlet there is a vertical distance of about 2 meters.

Apparatus constructed in accordance with the invention may also be employed for other fermentation processes by using appropriate substrates as raw material. Thus it may be used for the production of antibiotics, enzymes or even for biological treatment of sewage, as well as for the production of single-cell proteins on a base of hydrocarbon materials and methanol.

The invention will now be described by way of example with reference to the accompanying drawing.

IN THE DRAWING

DESCRIPTION OF EMBODIMENT IN THE DRAWING

Figure 1:
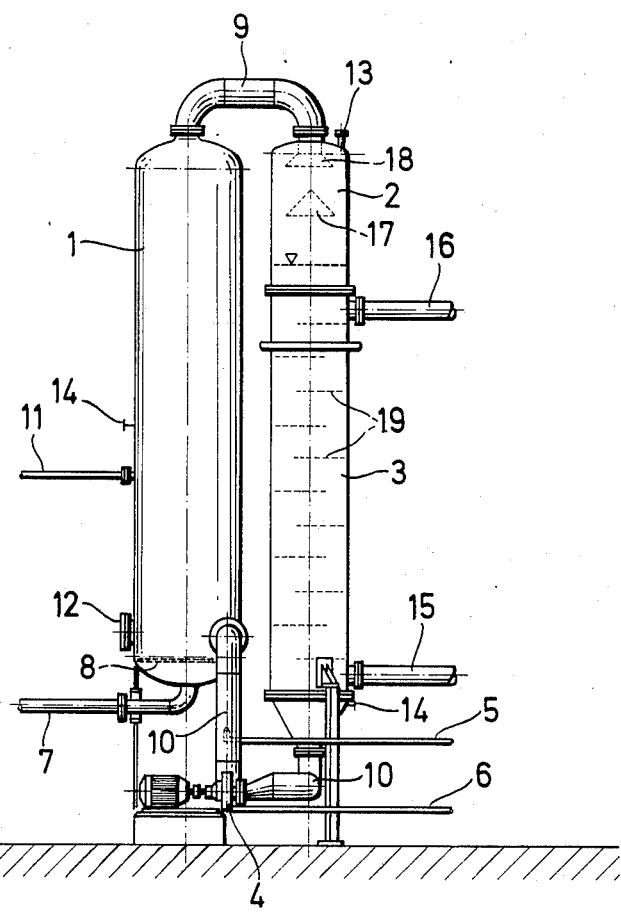
FIG. 1 is a schematic view, partly in cross-section, of a form of construction of the device according to the invention.
Figure 2:
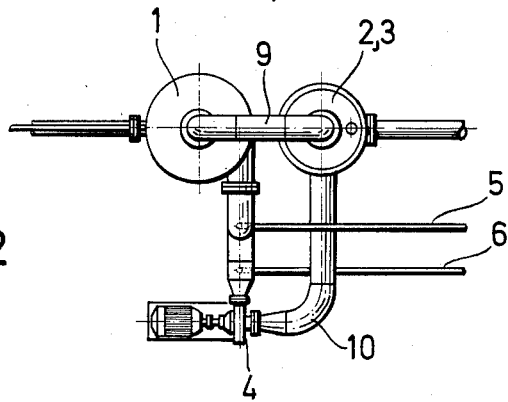
FIG. 2 is a plan view of the device depicted in FIG. 1.

A fermentation column 1 made, for example, of steel and preferably plated with high grade steel, has a capacity depending on its size, in the range 20 to 150 $m^3$. The column is kept filled with nutrient solution during operation by the circulation of the solution in the system. The solution is enriched with oxygen at the base of the column 1, the oxygen entering the column via an inlet pipe 7, and entering the solution through porous sintered plates from which the floor 8 is constructed. The sintered plates possess a pore-width of from 1 to 7 mu, preferably 3 mu.

A conduit 9 connects the top of the column 1 to the top of a second vessel the upper part of which consists of a gas-extraction chamber 2 and the lower part of which consists of a heat exchanger 3. The conduit 9 projects into the interior of the gas-extraction chamber 2 and ends in the form of a funnel 18. At this point liquid transferring from the column falls vertically downwards and it is at this point that the extraction of oxygen and carbon-dioxide from the liquid occurs. An outlet 13 for these gases in the form of exhaust air, is provided at the top of the gas-extraction chamber.

In order to increase the anti-foaming effect, a pyramid-shaped baffle device 17 is provided below the mouth 18 of the duct 9. The stream of culture medium strikes this and is thus dispersed in such a way that the gas content carried by it is released.

The heat resulting from the strongly exothermic fermentation process is removed from the culture medium within the heat exchanger 3. The latter includes a cooling water inlet 15 in which cold water is introduced, and a cooling water outlet 16 from which heated cooling water is removed. The heat exchange is effected by devices 19 in the heat exchanger 3 through which the cooling water flows.

The culture medium is led back into the column 1 through the conduit 10 which leaves the base of the heat exchanger 3.

The desired temperature is maintained by several pyrometers 14 and temperature-regulating devices (not shown).

A pump 4 situated in the conduit 10 circulates the nutrient solution at the desired speed.

In a known manner a preliminary fermentation column (not shown) and, if necessary, an interim fermentation column (not shown) can be connected to the main fermentation column 1. These additional columns serve to create the required amounts of inoculation material and nutrient solution which at the start of the process are introduced into the main column 1 through conduit 11. Thereafter the nutrient solution is poured in through inlet 5.

Outlet 6 allows the finished bio-mass to be extracted. This is situated directly downstream from the pump 4 and at a greater vertical distance of about 2 m below the inlet pipe 5.

The opening of the conduit 10 into the fermenter 1 is situated a little above the sintered plate base 8, and is arranged to one side in such a way that the culture medium flows tangentially into the fermentation column. A beneficial distribution and mixing of gas and liquid in the fermentation column 1 is achieved by means of the tangential entry of the fermentation liquid into the column, and the introduction of the oxygen in finely dispersed form.

The column has a manhole 12, through which the interior of the column is accessible for example for changing or maintaining the sintered plates forming the floor 8.

When the apparatus embodying the invention is used for the production of single-cell protein on a base of ethanol, the column 1 is first filled with yeast cultures, which have been cultivated either in a separate breeding-centre or in preliminary and interim columns (not shown). At the same time the heat exchanger 3 is filled with nutrient solution up to the level indicated by the open triangle shown in FIG. 1. The pump 10 is then switched on, causing the nutrient solution from the heat exchanger 3 to flow tangentially into the column 1.

During the fermentation process the liquid is pumped around in the required direction so that a complete change of liquid occurs 30 times per hour. Higher or lower rates of pumping in the range 10 to 100 complete changes per hour may be employed. Oxygen enrichment occurs in the region of the porous sintered plates 8 as a consequence of the introduction of oxygen through the inlet pipe 7. The time taken by the mixture of gas-liquid-solid to pass through the column 1 is preferably 0.6 $h^{-1}$. Thus with a column capacity of 20 $m^3$ and a circulation rate equivalent to 30 changes per hour, the mixture should pass through the column in 1.66 minutes.

The entry temperature into the column should be in the range 25° and 35° C., and the temperature at the column outlet should be in the range 35° to 40° C., preferably regulated to 39° C.

The fermentation process can be arranged on a batch basis or continuously. With batch operation the greatest micro-organism growth is reached within 12 to 20 hours after the start of fermentation, and the total content of the column is withdrawn after the appropriate time interval of 0.6 $h^{-1}$. With continuous fermentation, nutrient solution is introduced at the feed point 5 at the same rate as after yeast suspension is extracted from the withdrawal point 6.

In the course of batch fermentation it is possible, during the logarithmic growth phase of the micro-organism, to change to a continuous mode of operation with a corresponding time period.

With the device according to the invention it is possible to obtain high volume time yields and bio-mass concentration, and to achieve excellent quality of the end product. The energy consumption is comparatively low and the elimination of heat of reaction excellent.

The following example is given to illustrate the working of the invention:

The nutrient medium to be used is a mixture of the following:

| | |
|---|---|
| $KH_2PO_4$ | 2.0 ml |
| $(NH_4)_2SO_4$ | 0.2 g |
| $MgSO_4.7 H_2O$ | 1.0 g |
| Composite solution of other growth factors | 10.0 ml |
| diluted to give 1 liter of solution. | |

The composite solution is composed of the following:

| | |
|---|---|
| $CuSO_4.5 H_2O$ | 0.06 g |
| $ZnSO_4.7 H_2O$ | 1.0 g |
| $MnSO_4.H_2O$ | 0.4 g |
| $FeCl_3.6 H_2O$ | 5.2 g | diluted to give 1 liter of solution.

Ten percent synthetic ethanol is added to this nutrient medium which has a pH value of 3.5. Then a prepared culture of the yeast species Hansenula anomala is added as the inoculation medium and circulation of the nutrient medium into the column 1 is begun. Pure oxygen is introduced through the sintered plates 8 into the column in a vertical direction from below, in ultra-fine dispersion, with an average bubble-size of 3 mu, and at this point within the lower zone of the column the culture medium is introduced tangentially into the oxygen-enriched region of the column. With the relative movement of the tangentially introduced nutrient medium and finely dispersed gaseous oxygen, the desired gas-liquid-solid dispersion is obtained. With a column volume of 20 $m^3$ and a circulation rate of 30 changes per hour, the mixture takes 1.66 minutes to pass through the column 1.

The heat produced by the reactions within the yeast, is removed by means of cooling water. The entry temperature in the column amounts to some 33° C., and the exit temperature approximately 39° C.

The processing of the ethanol substrate by means of the yeast culture Hansenula is, in the first stage, initiated by the reduction of the ethanol to acetaldehyde by means of the alcohol-dehydrogenate enzymes. The resulting acetaldehyde enters the citric acid cycle by way of acetyl-coenzyme A. Through this cycle of tiscarboxyl acids, energy and hydrocarbon structures are established for the formation of the micro-organism.

The following results are achieved:

| | |
|---|---|
| Mean column temperature | approx. 35° C. |
| pH value | 3.5 |
| Substrate concentration | 0.01% |
| Time to traverse column | 0.6 $h^{-1}$ |
| Productivity | 45 kg/$m^3$ h |
| Substrate yield | 75% |
| Oxygen yield | 80% |

Productivity is based on dry yeast.

With a circulation rate of 600 $m^3$ per hour, 12 $m^3$ of culture medium can be extracted hourly and about 12 $m^3$ of fresh nutrient solution has to be introduced.

The protein content of the product obtained in this way amounts to some 70% of raw protein.

We claim:

1. A process for the microbiological production of single-cell protein on an ethanol substrate in a fermentation column, comprising the steps of:

supplying ethanol metabolizing yeasts which have been cultivated at temperatures of 20° to 40° C. under aerobic conditions to said fermentation column in a dilute nutrient medium having a pH value of 2.5 to 4;

constantly circulating a mixture comprised of said yeasts, said ethanol substrate and said nutrient medium into, through and out of the fermentation column during said process by pumping the mixture through the fermentation column;

tangentially introducing the mixture into a zone which is enriched with oxygen gas in said column during said step of circulating;

introducing oxygen into said column immediately below said zone;

forming said introduced oxygen into oxygen bubbles in the range of 1 to 7 microns; and supplying said oxygen bubbles upwardly to said zone substantially perpendicular to said tangentially introduced mixture to mix the oxygen bubbles with said mixture so as to form a stable dispersion of said mixture and said oxygen bubbles which can be conducted through said chamber at a relatively high speed without breaking up and effectively without the development of foam.

2. A process as set forth in claim 1; further including the step of extracting a gas evolved during fermentation within the fermentation column, from the mixture circulated out of the fermentation column.

3. A process as set forth in claim 1; further including the step of circulating the mixture through the fermentation column for a time period in the range 0.2 to 1.0 $h^{-1}$.

4. A process as set forth in claim 3; wherein the mixture passes through the fermentation column in a time period of 0.6 $h^{-1}$.

5. A process as set forth in claim 1; further comprising the step of exerting a positive pressure on the mixture which passes through the fermentation column so that any gas which evolves is carried away from the fermentation column before foam can form.

6. A process as set forth in claim 1; wherein the oxygen which is introduced into the column is pure oxygen.

7. A process as set forth in claim 1; further comprising the step of cooling the mixture circulated outside the fermentation column.

8. A process as set forth in claim 7; wherein said step of cooling the mixture includes the step of supplying said mixture to a heat exchange zone situated downstream and outside of the fermentation column.

9. A process as set forth in claim 8; further including the step of extracting a gas evolved during fermentation within the fermentation column, in a region upstream of the heat exchange zone and downstream and outside of the fermentation column.

10. A process as set forth in claim 1; wherein the pH value of the nutrient medium is 3.5.

11. A process as set forth in claim 1; wherein the step of forming includes the step of forming the oxygen introduced into the column to 3 microns.

12. Apparatus for the microbiological production of single-cell protein on an ethanol substrate in a fermentation column, comprising:

means for supplying ethanol metabolizing yeasts which have been cultivated at temperatures of 20° to 40° C. under aerobic conditions to said fermentation column in a dilute nutrient medium having a pH value of 2.5 to 4;

pump means for constantly circulating a mixture comprised of said yeasts, said ethanol substrate and said nutrient medium into, through and out of the fermentation column during said process;

means for tangentially introducing the mixture into a zone which is enriched with oxygen gas in said column when circulating the mixture;

means for introducing oxygen into said column immediately below said zone; and gas dispersion means for forming said introduced oxygen into oxygen bubbles in the range of 1 to 7 microns and for supplying said oxygen bubbles to said zone to mix the oxygen bubbles with said mixture so as to form a stable dispersion of said mixture and said oxygen bubbles which can be conducted through said column at a relatively high speed without breaking up and effectively without the development of foam.

13. Apparatus as set forth in claim 12; further comprising a separate heat exchanger, and upper and lower conduits connecting the column to the heat exchanger, the pump means being located in the lower conduit, and wherein said gas dispersion means produces finely dispered oxygen in a lower zone of the fermentation column.

14. Apparatus as set forth in claim 13; further comprising a gas extraction chamber located between the column and the heat exchanger, and a liquid inlet entering the gas extraction chamber vertically from above.

15. Apparatus as set forth in claim 14; further comprising inlet means in said chamber for auxiliary materials.

16. Apparatus as set forth in claim 14; further comprising a sampling valve in said chamber.

17. Apparatus as set forth in claim 14; wherein the gas extraction chamber and the heat exchanger are housed in a common vessel, the gas extraction chamber being situated above a heat exchange component in the vessel.

18. Apparatus as set forth in claim 13; further including outlet means for the bio-mass in fluid connection with the lower conduit and located downstream from said pump means.

19. Apparatus as set forth in claim 18; further including inlet means for the nutrient solution located in the lower conduit between the bio-mass outlet means and a junction of the lower conduit and the column.

20. Apparatus as set forth in claim 13; further including pyramid shaped baffle means positioned in said heat exchanger above the liquid level therein for releasing gases from said mixture as the latter strikes it when circulated to said heat exchanger from said fermenting column.

21. Apparatus as set forth in claim 12; wherein the gas dispersion means includes a porous plate having a pore size in the range 1 to 7 microns.

22. Apparatus as set forth in claim 12; wherein he gas dispersion means comprises at least one sintered plate.

* * * * *